United States Patent [19]

Cobb et al.

[11] Patent Number: 4,668,296

[45] Date of Patent: May 26, 1987

[54] ALKYLATION OF DIPHENYL OXIDE

[75] Inventors: R. Lynn Cobb; Michael D. Mitchell, both of Bartlesville, Okla.

[73] Assignee: Phillips Petroleum Company, Bartlesville, Okla.

[21] Appl. No.: 832,291

[22] Filed: Feb. 21, 1986

[51] Int. Cl.[4] .......................... C08L 1/08; C07C 41/00; C07C 43/02

[52] U.S. Cl. .................................... 106/188; 568/628; 568/635

[58] Field of Search ........................ 568/635; 106/188

[56] References Cited

U.S. PATENT DOCUMENTS

| | | |
|---|---|---|
| 2,170,809 | 8/1939 | Coleman et al. .................. 260/612 |
| 2,604,413 | 7/1952 | Kropscott et al. .................. 106/188 |
| 2,616,931 | 11/1952 | Rosenwald ..................... 568/628 |
| 3,003,889 | 10/1961 | Tamblyn ........................ 106/188 |
| 4,054,937 | 10/1977 | Mandelcorn et al. .............. 361/319 |
| 4,159,390 | 6/1979 | Klingel et al. ..................... 568/635 |

OTHER PUBLICATIONS

P. H. Groggins, Unit Processes in Organic Synthesis, 5th ed., McGraw-Hill, 1958, pp. 815–825.

*Primary Examiner*—Theodore Morris
*Attorney, Agent, or Firm*—French and Doescher

[57] ABSTRACT

An alkylated diphenyloxide composition is prepared by reacting diphenyloxide with isobutylene in the presence of sulfuric acid and applications for the composition.

19 Claims, No Drawings

ALKYLATION OF DIPHENYL OXIDE

BACKGROUND OF THE INVENTION

The present invention relates to alkylated diphenyloxide derivatives. In another aspect the invention relates to a specific method of making alkylated diphenyloxide derivatives, which method allows one to produce products having a wide range of viscosities.

Alkylated diphenyloxides have numerous applications such as dielectric agents in transformers, condensers, and other electrical equipment and as plasticizers, for resins, especially for cellulosic resins. Examples of some of such uses are disclosed in U.S. Pat. No. 2,604,413 and U.S. Pat. No. 4,054,937, the disclosures of which are incorporated herein by reference.

U.S. Pat. No. 2,170,809 of Coleman et al disclosed preparing such compounds by the reaction of a diphenylether with a diisobutylene in the presence of a Lewis acid "Friedel-Crafts" type catalyst, such as, for example, $AlCl_3$. U.S. Pat. No. 4,159,390 of Klingel et al discloses that a particular type of workup procedure allows one to obtain lower viscosity products than those reported in the literature for the Coleman et al products.

The present inventors have found that when an isoolefin is employed in excess with respect to the ether in the $AlCl_3$ catalyzed reaction, varying the molar ratio of the olefin to the ether has little significant effect on the viscosity of the final alkylated diphenyloxide. In addition, the present inventors have not found it possible to make alkylated diphenyloxide having the higher viscosities reported in U.S. Pat. No. 4,159,390 using $AlCl_3$ as the catalyst.

One object of the present invention is to provide a technique for the alkylation of diphenylether in which the viscosity of the material having a boiling point above 180° C. at 5 torr can be varied by varying the molar ratio of the iso-olefin to the ether.

Another object of the present invention is to provide a technique for producing alkylated diphenyl oxide that has a reasonably low pour point.

Still another object of the present invention is to provide a technique for readily separating the alkylated diphenylether from the reaction product mixture.

Still another object is to provide an alkylated diphenyloxide product useful as a plasticizer and as an electrical component.

SUMMARY OF THE INVENTION

In accordance with the present invention, alkylated diphenyloxide is produced by contacting a diphenyloxide with isobutylene in the presence of sulfuric acid under conditions such that tert-butyl groups are added to the diphenyloxide.

DETAILED DESCRIPTION

The term diphenyloxide is employed herein in both a generic and specific sense. Generically, it includes any compounds having two phenyl radicals connected by oxygen. Examples thus include diphenyloxide of the formula $C_{12}H_{10}O$ as well substituted diphenyloxides, such as partially alkylated diphenyloxides. Some specific examples include ethyl-diphenyloxide, di-isopropyl-diphenyloxide, isoamyl-diphenyloxide and di-isoamyl-diphenyloxide. For most applications the diphenyloxide used as a starting material would have 12 to 22 carbon atoms per molecule, more preferably 12 to 17 carbon atoms.

The catalyst for the reaction is sulfuric acid. Preferably a concentrated aqueous solution of $H_2SO_4$ is employed. Weaker acid solution can lead to undesired by-product formation. Typically the acidic liquid would contain about 88 to 99.3 weight percent $H_2SO_4$. The amount of acid employed can vary over a wide range but generally would be in the range of about 5 to about 50 volume percent based on the volume of the ether, or more preferably about 20 to about 40 volume percent.

The reaction is conducted under reaction conditions which allow for the production of the desired type of product. Typically, it is desirable to insure that the reaction is carried out at a temperature in the range of about 20° C. to 45° C., more preferably 25° C. to 35° C. The pressure is not considered to be critical.

The reaction is preferably carried out by combining the ether and at least a portion of the concentrated sulfuric acid. Then the isobutylene is added. In an especially preferred embodiment a portion of the acid catalyst is slowly added to the reaction mixture as the isobutylene is added. The addition rate of the olefin and cooling are used to keep the reaction mixture within the desired temperature range. After all the acid and olefin has been added the reaction mixture is generally maintained at a temperature in the range of 25° C. to 35° C. for a period of time to assure that the reaction is carried to the desired level of completion. Typically, this can be done by sampling the reaction product and determining the ratio of the amount of ether having two tertbutyl equivalents per molecule with the amount of ether having three tertbutyl equivalents per molecule. The optimum reaction time for a given reaction can thus be readily determined by routine experimentation. Preferably the reaction mixture is stirred during the reaction.

After the desired amount of reaction has occurred the aqueous acid layer can be separated from the product. The remaining product is then neutralized with a base, for example, a 15 weight percent solution of sodium hydroxide. Alternatively, the entire reaction mixture may be neutralized with base.

The ether product is then recovered from the neutralized mixture and is subjected to distillation to remove undesired light compounds. The addition of a salt such as sodium chloride can aid in the separation. In a preferred embodiment the recovered ether is stripped at about 180° C. at a pressure in the range of about 2 to 5 mm Hg.

In an especially preferred embodiment, a lower alcohol, such as methanol, ethanol, or isopropyl alcohol is added to the neutralization mixture. This has been found not only to increase the amount of the ether product that can be recovered but also to facilitate phase separation. Generally, the alcohol is employed in an amount of about 6 to about 12 percent of the weight of the product mixture after the acid layer had been removed but before the base solution had been added. The optimum amount of alcohol to be used can be determined by routine experimentation. Generally the use of a combination of alcohol and salt allows one to use lower levels of alcohol. Typically the separation is made at a temperature in the range of about 50° C. to 70° C. whether or not an alcohol is employed.

Once vacuum stripping is finished, the resulting product can be transferred while hot to a container for storage or the like.

In an especially preferred embodiment wherein the diphenyloxide that is alkylated has the formula $C_{12}H_{10}O$, the acid, the ether, and a methyl butene are combined prior to the introduction of the isobutylene. This has been found to provide a product of high viscosity with a low pour point, i.e., one that does not crystallize under ambient conditions. Most preferably, the ether is combined with about 10-15 volume percent of the concentrated sulfuric acid with stirring and then the methyl butene is added. After the butene has been added more of the concentrated sulfuric acid is slowly added with stirring while the isobutylene is being added.

The amount of isobutylene employed can vary over a wide range and the ratio of that olefin to the ether can affect the viscosity of the end product. Isobutylene to ether molar ratios in the range of about 4 to about 7 have been found to give products which after the vacuum distillation had viscosities at 25° C. in the range of about 1600 to over 8000 centipoise. Particularly desirable products have a viscosity in the range of about 4000 to 6000 centipoise.

The methyl butene, when employed could be basically any methyl substituted butene. Examples include 2-methyl-2 butene and neohexene. When the methyl butene is employed it is generally employed in an amount of about 10 to about 100 mole percent based on the ether, more preferably about 30 to 40 mole percent. The use of the methyl butene reduces the formation of materials which would lead to the formation of crystals or other solid substances which increase to an undesired level the pour point of the 180° C.+ material.

The process of the present invention is capable of providing alkylated diphenyloxide having particularly desirable properties. The process enables one to obtain a product having a much higher level of tri-tertbutyl substitution than the prior art processes. Products containing about 40 to about 50 volume percent tri-substitution are very typical. Such products also generally have about 10 to about 25 volume percent di-substitution and less than about 2 volume percent mono-substitution. One preferred type of product has the following properties:

Percent Transmission Through 1 cm of Sample at Wavelength of 450 nm:
At least 45%, more generally at least 95%.

Viscosity at 25° C. Using a CANNON-FENSKE Routine Viscometer to ASTM D445:
4700 CKS±500

Acid Number (The mg of KoH Required to Neutralize Free Acid is 1 gram of Product):
No more than 0.5.

Weight Percent Volatiles at 180° C. and 4 mm Hg for 1 hour:
No more than 9%, more generally less than 1%.

Specific Gravity at 25° C. as Determined in a Pycnometer Weighing Bottle:
0.92-0.95

Refractive Index at 15° C. in an Abbe Refractomer:
1.525±0.25

Garde Color by ASTM D1544:
No greater than 6

A further understanding of the present invention and its advantages over the prior art techniques will be provided by the following examples in which a diphenylether of the formula $C_{12}H_{10}O$ is alkylated.

EXAMPLE I

Using a procedure generally of the type as described in U.S. Pat. No. 2,170,809, diisobutylene (1.61 moles) was reacted with 0.36 moles of diphenylether in the presence of $AlCl_3$ at a temperature in the range of 50° to 55° C. A low viscosity product was obtained which was subjected to GLC analysis to reveal 16 volume percent monosubstitution, 14 volume percent disubstitution and 25 volume percent trisubstitution. (These terms referring to the relative amounts of mono-, di-, and tri-tert-butyl diphenylether in the product as shown by the areas under the respective GLC peaks.)

EXAMPLE II

In this run, 267 grams (1.57 moles) of diphenylether was mixed with 9 grams of $AlCl_3$ and stirred under nitrogen and isobutylene was added while the temperature of the mixture was maintained at about 60° C. The mole ratio of olefin to ether was 4.18. GLC analysis of the product revealed about 2 percent monosubstitution, about 41 percent disubstitution, and 20 percent trisubstitution. The resulting product while at 40° to 50° C. was washed once with dilute HCl and once with a 15 weight percent $NaCO_3$ solution. It was then filtered through celite and $MgSO_4$ and washed with aqueous caustic. Some pentane was added to add in phase separation. The organic product was separated and subjected to distillation at 180° C. and 3 mm Hg. The resulting product was a pale yellow oil of low viscosity.

EXAMPLE III

Another run was made as in Example II except that more isobutene was employed. In this run the molar ratio of the olefin to the ether was about 6.4/1. Analysis showed that the product had 2 percent mono, 31 percent di, and 27 percent tri substitution. Another low viscosity product was recovered substantially as in Example II. The viscosity in centipoise at 25° C. according to ASTM D445 was 918.

EXAMPLE IV

Attempts were also made to alkylate diphenylether with isobutene using several other Lewis acid type catalysts, namely $BF_3.H_3PO_4$, Amberlyst 15, and $H_3PO_4,P_2O_5$. All gave (stripped) products of low viscosity, e.g., in the range of 50 to 300 CPS at 25° C.

EXAMPLE V

A run was made by trying to alkylate diphenylether with diisobutylene, using sulfuric acid as the catalyst. The term diisobutylene as used herein refers to an isomer mixture comprising substantially 2,4,4-trimethyl-1-pentene. In this run 225 ml of diphenylether (1.42 moles) was combined with 10 ml of concentrated $H_2SO_4$ while at a temperature of about 30° C. To this mixture was added slowly 350 grams (6.25 mole) of the diisobutylene. An additional 25 ml of $H_2SO_4$ was added along with the isoolefin. The $H_2SO_4$ addition was begun 1 hour after the isoolefin addition was begun. The reaction mixture was maintained at about 30° C. The addition of the acid and the olefin was complete after 6 hours. The reactants were stirred for 1 more hour at about 30° C. GLC analysis revealed that the product contained about 5 percent of mono tert butyl product, 54 percent of the di tert butyl product and 4 percent of the tri tert butyl product. The reaction product was neutralized and the ether product separated and subjected to distillation at 180° C. and 3-4 mm Hg. The product boiling above 180° C. had a viscosity of 88 centipoise at 25° C.

EXAMPLE VI

A run was carried out similar to that of Example V using isobutylene rather than diisobutylene. In this case 225 ml of the ether was combined with 10 ml of sulfuric acid at about 27° C. Isobutylene addition was begun at a rate of 0.81 g/min. After the first hour the slow addition of more $H_2SO_4$ was also begun. The total addition of the isobutylene and extra acid was complete after six hours. The mixture was stirred for another hour at about 27° C. The total amount of isobutylene added was 6.75 mole and the total amount of additional acid was 25 ml. GLC analysis revealed less than 1 percent mono tertbutylated product, about 19 di tertbutylated, and about 63 tri tertbutylated. The product was worked up as before. The product boiling above 180° C. at 3-4 torr had a viscosity of 5600 centipoise at 25° C.

EXAMPLE VII

Another run was made like that of Example VI except that the molar ratio of the olefin to ether was 7.15 rather than 5.10. GLC showed less than 1 percent mono tertbutylated product, about 25 percent di tertbutylated product and about 57 percent tri tertbutylated product. The product boiling above 180° C. had a viscosity of 2447 centipoise at 25° C.

EXAMPLE VIII

Another series of runs were made in which diphenylether was reacted with isobutylene. However in these runs a mixture of the ether and the acid was combined with 2-methyl-2-butene prior to the addition of the isobutylene. The temperature was maintained in the range of about 25° to 35° C. The general procedure used involved combining the ether and a portion of the acid, adding the methyl butene over the period of about an hour and then slowly adding the isobutylene and more acid over five hours. Stirring was continued for 1 hour after all the isobutene had been added. The results are summarized in the following Table.

TABLE I

Example Showing Alcohol Treatment

| Run | iC4* | 2MB2* | GLC % Selectivity Mono | Di | Tri | Viscosity** |
|---|---|---|---|---|---|---|
| 1 | 435 | 34 | <1 | 14 | 48 | 4296 |
| 2 | 445 | 34 | <1 | 15 | 46 | 5579 |
| 3 | 490 | 34 | <1 | 10 | 42 | 7409 |
| 4 | 500 | 34 | <1 | 15 | 47 | 3983 |
| 5 | 665 | 36 | <1 | 19 | 42 | 2618 |
| 6 | 674 | 36 | <1 | 16 | 43 | 4952 |

*Mole percent based on the moles of ether.
**Centipoise at 25° C. (ASTM D445).

This data show that the inventive process is capable of producing a wide range of higher viscosity alkylated diphenyl ethers. It further shows that the inventive process is capable of producing stripped products having much higher viscosities than the stripped products produced using an $AlCl_3$ catalyzed reaction.

That which is claimed:

1. A method for preparing an alkylated diphenyloxide comprising contacting a diphenyloxide with isobutylene in the presence of sulfuric acid under conditions such that tert-butyl groups are added to the diphenyloxide
wherein about 40 to 60 volume percent of the product is either having tri tertiary butyl substitution and 10 to 25 volume percent is ether having di tertiary butyl substitution.

2. A method according to claim 1 wherein said diphenyloxide has 12 to 22 carbon atoms per molecule.

3. A method according to claim 2 in which diphenyloxide of the formula $C_{12}H_{10}O$ is alkylated.

4. A method according to claim 3 wherein the contacting is conducted at a temperature in the range of about 25° to about 35° C.

5. A method according to claim 4 wherein the reaction product mixture is neutralized, the alkylated diphenyloxide is separated from the aqueous portion, and the alkylated diphenyloxide is subjected to vacuum distiilation at 180° C. at a pressure in the range of about 2 to 5 mm Hg.

6. A method according to claim 5 wherein the distillation is conducted until a product is obtained that has no more than about 9 weight percent volatiles when subjected to vacuum distillation at 180° C. and 4 mm Hg for one hour.

7. A method according to claim 6 wherein the product has a viscosity at 25° C. in the range of about 1600 to about 6000 centipoise.

8. A method according to claim 7 wherein the molar ratio of the isobutylene contacted with the diphenyloxide is in the range of about 4/1 to about 7/1.

9. A method according to claim 8 wherein said diphenyloxide is contacted with 2-methyl-2-butene in the presence of sulfuric acid under conditions such that alkylation occurs prior to the contacting of the diphenyloxide with the isobutylene.

10. A method according to claim 8 wherein the product mixture after being neutralized is contacted with alcohol to assist in the breaking of the resulting emulsion so that the ether can be separated from the aqueous component.

11. Alkylated diphenyloxide produced by the process of claim 1.

12. A composition comprising alkylated diphenyloxide wherein about 40 to 60 percent of the composition is diphenyloxide having tri tertbutyl substitution and about 10 to 25 percent of the composition is diphenyloxide having di tertbutyl substitution.

13. A composition according to claim 12 having no more than about 9 weight percent volatiles when subjected to vacuum distillation at 180° C. and 4 mm Hg for one hour.

14. A composition according to claim 13 having a viscosity at 25° C. in the range of 4000 to 6000 centipoise.

15. A composition of matter comprising ethyl cellulose and a plasticizing amount of the alkylated diphenyloxide composition of claim 14.

16. A composition according to claim 15 wherein said alkylated diphenyloxide composition is about 2 to 30 percent by weight of the total composition.

17. An explosive device containing a detonation mechanism comprising an inhibitor strip containing the alkylated diphenyloxide composition of claim 14.

18. An electrical transformer containing the alkylated diphenyloxide composition of claim 13.

19. An electrical condensor containing the alkylated diphenyloxide composition of claim 13.

* * * * *